US010093551B2

(12) United States Patent
Hammon et al.

(10) Patent No.: US 10,093,551 B2
(45) Date of Patent: Oct. 9, 2018

(54) PROCESS AND PLANT FOR TREATMENT OF SECONDARY COMPONENTS OBTAINED IN ACROLEIN AND/OR (METH)ACRYLIC ACID PRODUCTION

(71) Applicant: BASF SE, Ludwigshafen (DE)

(72) Inventors: Ulrich Hammon, Mannheim (DE); Thomas Walter, Hassloch (DE); Christian Raith, Mannheim (DE)

(73) Assignee: BASF SE, Ludwigshafen (DE)

( * ) Notice: Subject to any disclaimer, the term of this patent is extended or adjusted under 35 U.S.C. 154(b) by 237 days.

(21) Appl. No.: 14/857,998

(22) Filed: Sep. 18, 2015

(65) Prior Publication Data
US 2016/0083267 A1 Mar. 24, 2016

Related U.S. Application Data

(60) Provisional application No. 62/053,810, filed on Sep. 23, 2014.

(30) Foreign Application Priority Data

Sep. 23, 2014 (DE) .......................... 10 2014 113 699

(51) Int. Cl.
*C02F 1/04* (2006.01)
*B01D 1/00* (2006.01)
(Continued)

(52) U.S. Cl.
CPC ............ *C02F 1/048* (2013.01); *B01D 1/0058* (2013.01); *B01D 3/26* (2013.01); *B01D 3/346* (2013.01);
(Continued)

(58) Field of Classification Search
CPC .. C02F 1/048; C02F 2303/10; C02F 2103/36; C02F 1/16; B01D 3/26; B01D 1/0058;
(Continued)

(56) References Cited

U.S. PATENT DOCUMENTS 3,926,744 A * 12/1975 Noll ...................... C07C 45/783
203/55
3,932,500 A * 1/1976 Duembgen ........... C07C 51/252
562/600
(Continued)

FOREIGN PATENT DOCUMENTS

DE 2 136 396 C3 10/1974
DE 2449780 A1 * 4/1976 ............. C07C 51/48
(Continued)

*Primary Examiner* — Amber R Orlando
*Assistant Examiner* — Stephen Hobson
(74) *Attorney, Agent, or Firm* — Oblon, McClelland, Maier & Neustadt, L.L.P.

(57) ABSTRACT

The present invention relates to a process for treating secondary components obtained in acrolein and/or (meth) acrylic acid production, comprising the steps of:

Figure 1:
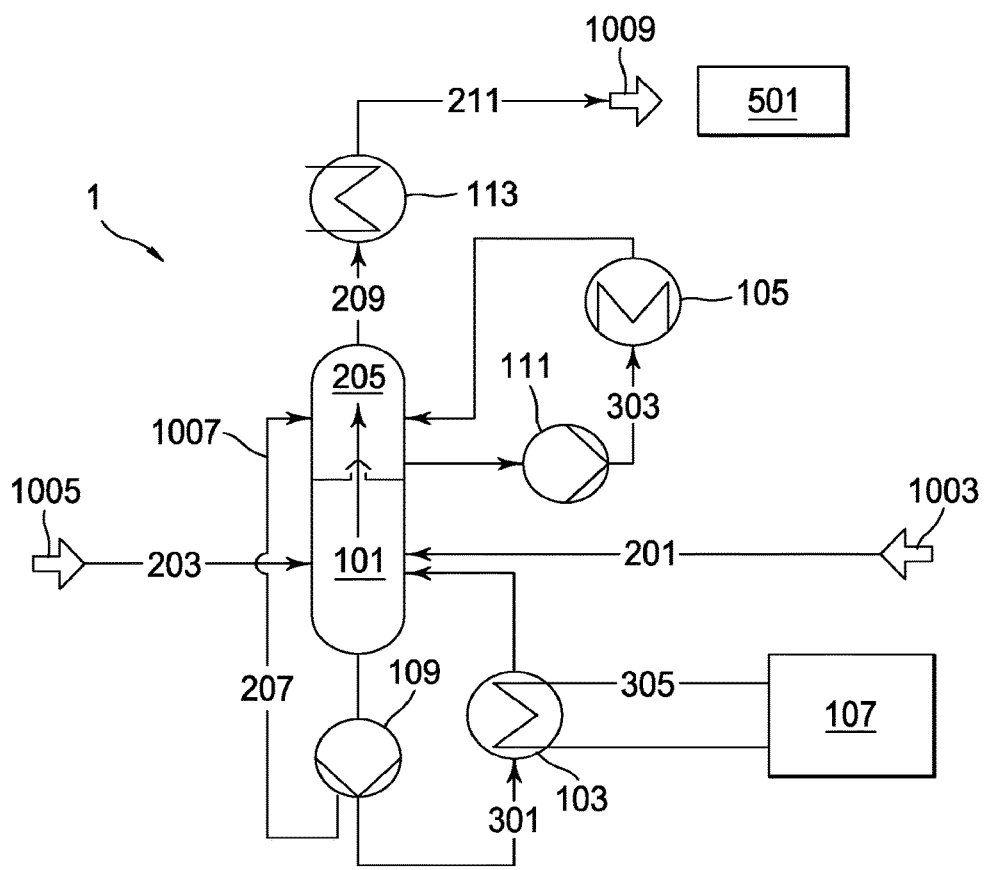

a) contacting at least one wastewater stream (201) comprising at least a portion of the water of reaction removed in a first stage of a saturation column (101) with at least one process offgas stream (203), b) introducing energy by means of a first heat transferer (103) provided in a first saturation circuit (301) into the first stage of the saturation column (101), c) partly vaporizing the wastewater stream (201) into the process offgas stream (203) and passing the combined gas stream (205) into a second stage of the saturation column (101), d) drawing off a concentrated wastewater stream (207) from the bottom (1011) of the first stage of the saturation column (101) and feeding it to the top (1023) of the second stage of the saturation column (101), e) introducing energy by means of a second heat transferer (105) provided in a second circuit (303) into the second stage of the saturation column (101), f) partly vaporizing the concentrated wastewater stream (207) into the combined gas stream (205) to obtain an offgas stream (209), (Continued)

g) superheating the offgas stream (209), after it has been saturated, in a third heat transferer (113) to obtain a superheated offgas stream (211) and h) transferring the offgas stream (209) or the superheated offgas stream (211) from the saturation column (101) to a thermal aftertreatment.

The present invention further relates to a plant (1) for treating the secondary components obtained in acrolein and/or (meth)acrylic acid production.

6 Claims, 2 Drawing Sheets

(51) Int. Cl.
*B01D 3/26* (2006.01)
*C07C 51/44* (2006.01)
*B01D 3/34* (2006.01)
*C07C 57/04* (2006.01)
*C02F 1/16* (2006.01)
*C02F 103/36* (2006.01)

(52) U.S. Cl.
CPC ............ *C02F 1/16* (2013.01); *C02F 2103/36* (2013.01); *C02F 2303/10* (2013.01); *C07C 51/44* (2013.01); *C07C 57/04* (2013.01); *Y02W 10/30* (2015.05)

(58) Field of Classification Search
CPC ......... B01D 3/346; C07C 57/04; C07C 51/44; Y02W 10/30
See application file for complete search history.

(56) References Cited

U.S. PATENT DOCUMENTS

| | | | | |
|---|---|---|---|---|
| 3,962,074 A * | 6/1976 | Schropp | ............... | C07C 51/48 210/634 |
| 5,315,037 A * | 5/1994 | Sakamoto | ............... | C07C 51/46 562/545 |
| 5,426,221 A * | 6/1995 | Willersinn | ......... | B01D 53/1493 562/600 |
| 5,817,865 A * | 10/1998 | Machhammer | ......... | C07C 51/43 560/208 |
| 6,515,187 B1 * | 2/2003 | Schon | ............... | C07C 45/82 568/492 |
| 6,676,808 B2 * | 1/2004 | Hamamoto | ............ | B01D 3/322 203/2 |
| 6,679,939 B1 * | 1/2004 | Thiel | ................. | B01D 3/14 202/158 |
| 7,557,245 B2 * | 7/2009 | Nordhoff | ................ | C07C 51/43 562/600 |
| 7,622,607 B2 * | 11/2009 | Fauconet | ................ | C07C 51/42 562/600 |
| 7,632,968 B2 * | 12/2009 | Kang | ...................... | C07C 51/44 562/600 |
| 8,128,787 B2 * | 3/2012 | Wynn | ................. | B01D 53/228 203/12 |
| 9,005,532 B2 * | 4/2015 | Baek | .................... | C07C 51/252 422/129 |
| 9,090,548 B2 * | 7/2015 | Cerda Baro | ............ | C07C 51/02 |
| 9,150,483 B2 * | 10/2015 | Huetten | ................ | C07C 51/252 |
| 9,745,244 B2 * | 8/2017 | Ligon | ..................... | C07C 51/44 |
| 2005/0192464 A1 * | 9/2005 | Kang | ...................... | C07C 51/48 562/600 |
| 2011/0172462 A1 * | 7/2011 | Ligon | ..................... | C07C 51/44 562/600 |
| 2012/0226074 A1 * | 9/2012 | Ho | .......................... | C07C 51/44 562/600 |
| 2014/0005437 A1 * | 1/2014 | Zacchi | ................... | C07C 45/28 568/63 |
| 2014/0018570 A1 * | 1/2014 | Pazicky | .................. | C07C 51/09 562/517 |
| 2014/0162345 A1 * | 6/2014 | Eyal | ......................... | C08H 8/00 435/253.6 |
| 2015/0353460 A1 * | 12/2015 | Boeck | ..................... | C07C 45/35 568/476 |
| 2016/0090347 A1 * | 3/2016 | Hammon | ............... | B01D 3/346 562/598 |
| 2017/0320804 A1 * | 11/2017 | Ligon | ..................... | B01D 3/42 |

FOREIGN PATENT DOCUMENTS

| | | | |
|---|---|---|---|
| DE | 23 23 328 C2 | 4/1982 | |
| DE | 24 49 780 C3 | 1/1987 | |
| DE | 43 08 087 A1 | 9/1994 | |
| EP | 0 551 111 A1 | 7/1993 | |
| JP | 2014-133719 | * 7/2014 | |
| JP | 5998063 B2 | * 9/2016 | |
| WO | WO-2005049541 A2 | * 6/2005 | ............ C07C 51/44 |
| WO | WO2017111277 | * 6/2017 | |

* cited by examiner

PROCESS AND PLANT FOR TREATMENT OF SECONDARY COMPONENTS OBTAINED IN ACROLEIN AND/OR (METH)ACRYLIC ACID PRODUCTION

This patent application claims the benefit of U.S. provisional patent application Ser. No. 62/053,810 and DE patent application Serial Number DE 10 2014 113 699.3, both filed on Sep. 23, 2014, incorporated in their entirety herein by reference.

The present invention relates to a process and to a plant for treatment of secondary components obtained in acrolein and/or (meth)acrylic acid production.

Acrolein, acrylic acid and methacrylic acid are important commodity chemicals. Because it has a very reactive double bond and an acid function, acrylic acid is suitable, especially as a monomer, for preparation of polymers. The greater part of the volume of acrylic acid monomers produced is esterified prior to the polymerization (for example to give adhesives, dispersions or coating materials). Only the smaller part of the acrylic acid monomers prepared is polymerized directly (for example to give "superabsorbents"). While monomers of high purity are generally required in the direct polymerization of the acrylic acid, the demands on the purity of acrylic acid are not so high if it is esterified prior to the polymerization.

It is common knowledge that acrylic acid or methacrylic acid can be prepared in two stages via acrolein or methacrolein by heterogeneously catalyzed gas phase oxidation of propene or isobutene with molecular oxygen over catalysts in the solid state at temperatures between 200° C. and 400° C. This is done using oxidic multicomponent catalysts, for example based on oxides of the elements molybdenum, chromium, vanadium or tellurium. Subsequently, the reaction product formed in the oxidation is absorbed into a low-boiling solvent, preferably water, or a high-boiling solvent, and the acrylic acid or methacrylic acid is subsequently removed by distillation and/or extraction. After this separation, the (meth)acrylic acid can optionally be purified further by crystallization.

In addition, it is also possible to condense the gaseous reaction product which comprises water and is formed in the oxidation, giving an aqueous acrolein or (meth)acrylic acid solution, from which the acrolein or the (meth)acrylic acid is separated in turn by distillation and/or extraction.

DE 21 36 396 C discloses, for example, separation of acrylic acid from the reaction gases obtained in the catalytic oxidation of propene or acrolein by countercurrent absorption with a mixture of 75% by weight of diphenyl ether and 25% by weight of diphenyl. Moreover, DE 24 49 780 C3 discloses the cooling of the reaction gas by partial evaporation of the solvent in a direct condenser prior to the countercurrent absorption. A problem here and in further process steps is the occurrence of solids in the apparatuses, which reduces plant availability. According to DE 43 08 087 A1, the level of solids that occurs can be reduced by adding a polar solvent such as dimethyl phthalate in an amount of 0.1% by weight to 25% by weight to the relatively nonpolar solvent mixture of diphenyl ether and diphenyl (called "Diphyl").

As well as the above-described absorption of the reaction product comprising acrylic acid into a high-boiling solvent (or solvent mixture), there also exist other process principles. The above-described process differs from the other processes in that the acrylic acid is absorbed here in substantially anhydrous form into a high-boiling solvent (or solvent mixture). The water is drawn off from the process in a separate process section. Other processes provide for total condensation of acrylic acid and additionally water of reaction formed in the catalytic oxidation. This forms an aqueous acrylic acid solution which can be worked up further via distillation with an agent which forms an azeotrope with acrylic acid, or via an extraction process. In EP 0 551 111 A1, for example, the mixture of acrylic acid and by-products prepared by means of catalytic gas phase oxidation is contacted with water in an absorption tower, and the aqueous solution obtained is distilled in the presence of a solvent which forms an azeotrope with polar low boilers such as water or acetic acid. DE 23 23 328 C describes the separation of acrylic acid from an aqueous acrylic acid esterification waste liquor or an aqueous acrylic acid solution as formed in acrylic acid production by oxidation of propene or acrolein, by extraction with a specific mixture of organic solvents.

A common factor to all processes utilized industrially for preparation of acrolein and/or (meth)acrylic acid is that low boilers, medium boilers and high boilers are obtained as unwanted secondary components and hence as streams for disposal. These at least three streams constitute a considerable cost burden to the process, since, according to the prior art, they are combusted in a thermal aftertreatment plant using energy carriers (generally natural gas), which leads to a high energy demand.

It is therefore an object of the present invention to specify a process for treating secondary components obtained in acrolein and/or (meth)acrylic acid production, and to provide a corresponding plant, which lower the requirement for energy carriers and hence constitute an economically efficient and environmentally optimal solution for the treatment of the secondary components.

In a first aspect, the invention relates to a process for treating secondary components obtained in acrolein and/or (meth)acrylic acid production, comprising the steps of:

a) contacting at least one acid water stream (201) comprising at least a portion of the water of reaction removed in a first stage of a saturation column (101) with at least one process offgas stream (203), b) introducing energy by means of a first heat transferer (103) provided in a first saturation circuit (301) into the first stage of the saturation column (101), c) partly vaporizing the acid water stream (201) into the process offgas stream (203) and passing the combined gas stream (205) into a second stage of the saturation column (101), d) drawing off a concentrated acid water stream (207) from the bottom (1011) of the first stage of the saturation column (101) and feeding it to the top (1023) of the second stage of the saturation column (101), e) introducing energy by means of a second heat transferer (105) provided in a second saturation circuit (303) into the second stage of the saturation column (101), f) partly vaporizing the concentrated acid water stream (207) into the combined gas stream (205) to obtain an offgas stream (209), g) superheating the offgas stream (209), after it has been saturated, in a third heat transferer (113) to obtain a superheated offgas stream (211) and h) transferring the offgas stream (209) or the superheated offgas stream (211) from the saturation column (101) to a thermal aftertreatment (501).

In a second aspect of the invention, the invention relates to a plant (1) for treating secondary components obtained in acrolein and/or (meth)acrylic acid production, comprising an at least two-stage saturation column (101),
a first feed (1003) for a wastewater stream (201)
a second feed (1005) for a process offgas stream (203),
a first saturation circuit (301) having a first pump (109) and a first heat transferer (103),
a conduit (1007) for a concentrated wastewater stream (207) from the bottom (1011) of the first stage of the saturation column (101) to the top (1023) of the second stage of the saturation column (101),
a second saturation circuit (303) having a second pump (111) and a second heat transferer (105) and
an outlet (1009) provided above the top (1023) of the saturation column (101) for an offgas stream (209).

Through the method of the invention and with the plant (1) of the invention, it is possible, in acrolein and/or (meth)acrylic acid production, to treat the secondary components obtained, for example acid water, such that they can be disposed of efficiently. More particularly, the acid water stream obtained in acrolein and/or (meth)acrylic acid production is converted substantially to the gas phase before it is sent to a thermal aftertreatment unit.

The present invention is described in detail hereinafter.

It has been found that, surprisingly, the aforementioned object is achieved, in a first aspect of the invention, by a process for treating secondary components obtained in acrolein and/or (meth)acrylic acid production. This process comprises, in a first step a), the contacting of at least one acid water stream (201) comprising at least a portion of the water of reaction removed in a first stage of a saturation column (101) with at least one process offgas stream (203) and, in a second step b), the introduction of energy by means of a first heat transferer (103) provided in a first saturation circuit (301) into the first stage of the saturation column (101).

Subsequently, in a step c), the acid water stream (201) is partly vaporized into the process offgas stream (203) and the combined gas stream (205) is passed on into a second stage of the saturation column (101). From the bottom (1011) of the first stage of the saturation column (101), in a step d), a concentrated acid water stream (207) is drawn off and the latter is fed to the top (1023) of the second stage of the saturation column (101).

In a step e), energy is introduced by means of a second heat transferer (105) provided in a second saturation circuit (303) into the second stage of the saturation column (101), and then, in a step f), the vaporization of the concentrated acid water stream (207) into the combined gas stream (205) is executed to obtain an offgas stream (209).

In a step g), the offgas stream (209), after leaving the saturation region of the saturation column (101), is superheated in a heat transferer (113) to obtain a superheated offgas stream (211). In a final step, step h), the offgas stream (209) or the superheated offgas stream (211) is transferred from the saturation column (101) to a thermal aftertreatment (501).

The present invention provides an efficient process for treating secondary components obtained in acrolein and/or (meth)acrylic acid production, especially for disposal of acid water, with simultaneous saving of energy.

Through the contacting of the acid water stream (201) with the process offgas stream (203), the vaporization of the acid water stream (201) is promoted by lowering of the partial pressure, i.e. by the dilution of the acid water stream (201) with the fraction of inert gases in the process offgas stream (203). In addition, in step b), energy is introduced into the system from outside, more specifically via a first saturation circuit (301), in order to achieve the desired degree of evaporation.

In the present description, the terms "high boilers", "medium boilers" and "low boilers", and corresponding terms used as adjectives, refer, respectively, to compounds having a higher boiling point than the acrylic acid or methacrylic acid ("high boilers") and to those having about the same boiling point as acrylic acid or methacrylic acid ("medium boilers") and to those having a lower boiling point ("low boilers").

In the present description, "acid water" is understood to mean the condensate which arises when the reaction gas which is not absorbed in the absorption of acrylic acid and/or methacrylic acid is cooled after the absorption, in order to separate the condensable portion of the low-boiling secondary components therefrom, especially water, formaldehyde and acetic acid, by condensation. The acid water thus comprises the secondary components which are dissolved in water and are to be disposed of, especially the water formed in acrolein and/or (meth)acrylic acid production and water-soluble low boiler and medium boiler components.

The acid water stream (201) comprises low- or medium-boiling secondary components which are dissolved in water and are to be disposed of, preferably comprising 0.1% by weight to 10% by weight of acetic acid, 0.01% by weight to 5% by weight of maleic acid, 0.01% by weight to 8% by weight of fumaric acid, 0.2% by weight to 4% by weight of formaldehyde and/or 0.1% by weight to 10% by weight, preferably 5% by weight, of other organic material such as formic acid, propionic acid, benzaldehyde, diacrylic acid, hydroxypropionic acid, benzoic acid and/or diphenyl ether (residues thereof when used as solvent), based in each case on 100% by weight of the secondary components. Typically, these secondary components comprise acetic acid, maleic acid and formaldehyde.

The high-boiling secondary components comprise, as well as 0.1% by weight to 10% by weight of (meth)acrylic acid, predominantly acrylic acid polymers and/or methacrylic acid polymers, unconsumed production stabilizers, for example phenothiazine, hydroquinone, hydroquinone monomethyl ether or p-nitrosophenol, and/or the thermal degradation products thereof. The acid water stream (201) is obtained in acrolein purification as a high boiler stream in the bottom (1011) of the absorption column (101), and in the (meth)acrylic acid purification as a low boiler stream at the top (1023) of the absorption column (101).

The process offgas stream (203) comprises gaseous low-boiling secondary components which, as well as the gaseous secondary components obtained in the acrolein and/or (meth)acrylic acid production, also include low-boiling liquid components (liquid at room temperature) which essentially comprise, as well as inert gases such as nitrogen, also water, carbon monoxide and carbon dioxide, the low boiler fraction of the substances to be disposed of, preferably (meth)acrolein, acetaldehyde, propane, propene, isobutene, formaldehyde, formic acid and/or reactants unconverted in the acrolein and/or (meth)acrylic acid production.

In a development of the process of the invention, energy is introduced in step b) by coupling the first heat transferer (103) with a stream available in the process for acrolein and/or (meth)acrylic acid production. In this way, low-value energy can be introduced into the process and higher-value energy, which generally entails the combustion of energy carriers, can be saved.

More particularly, the stream present in the process for acrolein and/or (meth)acrylic acid production is an acid water circulation stream (305) from an absorption column (107).

Alternatively, the stream present in the process for acrolein and/or (meth)acrylic acid production may be a circulation stream from the condensation circuit of a distillation column.

The heat from this acid water circuit (305) or this circulation stream has to date been unutilized waste heat which had to be removed by means of appropriate coolers. Through the process of the invention, this waste heat can be introduced into the treatment of the secondary components obtained.

As well as the efficient exploitation of the energy available in the process, it is possible to save further energy elsewhere in the process, since the burden on coolers needed for the acid water circuit (305) can be reduced and they can optionally be designed in a smaller size.

It is preferable when essentially water is circulated in the first saturation circuit (301) via the first heat transferer (103) and the first stage of the saturation column (101). This water is especially acid water consisting to an extent of about 91% of water, and additionally significant proportions of acetic acid and acrylic acid, and also small residues of formaldehyde, acrolein, allyl formate, formic acid and diphenyl ether. Since the acid water is a highly dilute solution of organic acids and low-boiling aldehydes, the stream in the circuit (301) can be concentrated without any great risk of formation of deposits and/or fouling products.

In a development, it is further preferable when the introduction of energy in step e) is effected by coupling the second heat transferer (105) with a heating medium stream. This heating medium stream may especially be low-pressure steam. This achieves very substantial vaporization of the acid water stream (201).

It is particularly advantageous when at least one further stream is present in the process, which has to be cooled from a higher temperature than the heating stream for the first saturation circuit to a lower temperature. For this purpose, it is possible to use the effluent stream from the distillation column in the example of DE 43 08 087 A1, this consisting essentially of diphenyl ether and, before being supplied to the absorption column, having to be cooled from a temperature of 190° C. to about 50° C. This amount of energy to be removed from the stream can be introduced into the system via the second saturation circuit (303) via the heat exchanger (105) through further evaporation of acid water.

For the efficiency of the process of the invention, it has been found to be advantageous when, in step c), at least 20% of the acid water stream (201) is vaporized, preferably at least 30%, more preferably at least 40% and especially at least 50%. The higher the level of vaporization of the acid water stream (201), the more higher-value energy can be saved and replaced by low-value energy.

In a preferred embodiment, by virtue of the thermal integration of low-value waste heat available in the process, at least 50% of the acid water stream (201) can be vaporized. Much higher vaporization levels can be achieved only with difficulty with this embodiment, since the rising boiling temperature of the residual liquid in the acid water stream (201) (for example through the enrichment of high boilers) results in a smaller driving temperature gradient against the waste heat from the acid water circuit (305). In a specific embodiment, the acid water circuit (305) has a temperature of 61.2° C. In order to achieve the aforementioned higher concentration levels, a much greater heat exchange area would have to be provided, which does not appear to be economically viable.

According to the invention, therefore, a two-stage concept is implemented, in which, in the first stage, at least 50% of the acid water stream (201) is first vaporized by means of the described thermal integration of waste energy. In a second stage, the residual liquid in the acid water stream (201) is vaporized via the introduction of conventional heat from a heating medium, for example steam.

In the case of vaporization levels higher than 70% over the two vaporization circuits, there is the risk that the solubility limit of dissolved organic substances such as maleic acid or phthalic acid will be reached, and the precipitating substances will build up deposits in the vaporization circuit, or that polymerizable substances such as acrolein, acrylic acid or (meth)acrylic acid will become enriched in the acid water to such an extent that they form higher oligomers or polymers that cover the heat exchange surfaces.

The aforementioned object is also achieved, in a second aspect of the invention, by a plant (1) for treating secondary components obtained in acrolein and/or (meth)acrylic acid production. This plant (1) comprises, as the central constituent, an at least two-stage saturation column (101) provided with a first feed (1003) for an acid water stream (201) and a second feed (1005) for a process offgas stream (203).

The plant (1) further comprises a first saturation circuit (301) having a first pump (109) and a first heat transferer (103), a conduit (1007) for a concentrated acid water stream (207) from the bottom (1011) of the first stage of the saturation column (101) to the top (1023) of the second stage of the saturation column (101), a second saturation circuit (303) having a second pump (111) and a second heat transferer (105) and an outlet (1009) provided above the top (1023) of the saturation column (101) for an offgas stream (209). This offgas stream (209) is sent to a thermal aftertreatment plant.

The plant of the invention has essentially the same advantages as the above-described process of the invention. More particularly, a plant (1) for efficient treatment of secondary components obtained in acrolein and/or (meth)acrylic acid production is provided, especially for substantial conversion of the acid water stream obtained in the acrolein and/or (meth)acrylic acid production to the gas phase.

In the context of the present invention, "saturation column" is understood to mean a column in which a gas stream is contacted with a liquid in countercurrent virtually until the gas/liquid thermodynamic equilibrium is attained.

The saturation column (101) may have various designs, for example as a countercurrent apparatus with a bed of random packing, as a countercurrent apparatus with spray nozzles (1015), as a cocurrent apparatus with spray nozzles (1015) and a separation vessel, or as a cocurrent apparatus with a cyclone separator. According to the invention, particular preference is given to a combination of two designs, since neither soiling nor biphasicity is to be expected in the first stage of the vaporization of the acid water stream (201), whereas both can occur in the second stage. Specifically, a bed of random packing (1013) is provided for the first stage, while a countercurrent spray tower (1017) is employed for the second stage. Above the second stage, a droplet separator (1021) is provided, which undertakes at least a coarse removal. In order to minimize apparatus complexity, the two stages can be combined in a single saturation column (101), in which case the two stages are separated by a collecting tray. This collecting tray can additionally assume the function of the pump reservoir.

In a development of the plant (1) of the invention, the first heat transferer (103) of the first saturation circuit (301) is coupled with a stream present in the process for acrolein and/or (meth)acrylic acid production, especially an acid water circulation stream (305) from an absorption column (107).

In an alternative development, the first heat transferer (103) in the first saturation circuit (301) may be coupled to a stream available in the process for acrolein acid and/or (meth)acrylic acid production, especially a condensation circulation stream from a distillation column.

This coupling according to the alternative embodiments makes it possible to introduce low-value energy into the plant (1) in the form of waste heat, and hence to save higher-value energy.

In a preferred embodiment, the plant (1) further comprises a third heat transferer (113) disposed above the top (1023) of the saturation column (101) in the outlet (1009). This third heat transferer (113) serves to superheat the gas stream (209) withdrawn from the saturation column (101), and thus to avoid condensation of condensable gas constituents in the gas stream (209) from the saturation column (101) to the downstream thermal aftertreatment unit.

Further aims, features, advantages and possible uses will be apparent from the description of working examples of the invention that follows, with reference to the figures. All the features described and/or shown in pictorial form, alone or in any combination, form the subject matter of the invention, even independently of the combination thereof in the claims or their dependency references.

Figure 2:
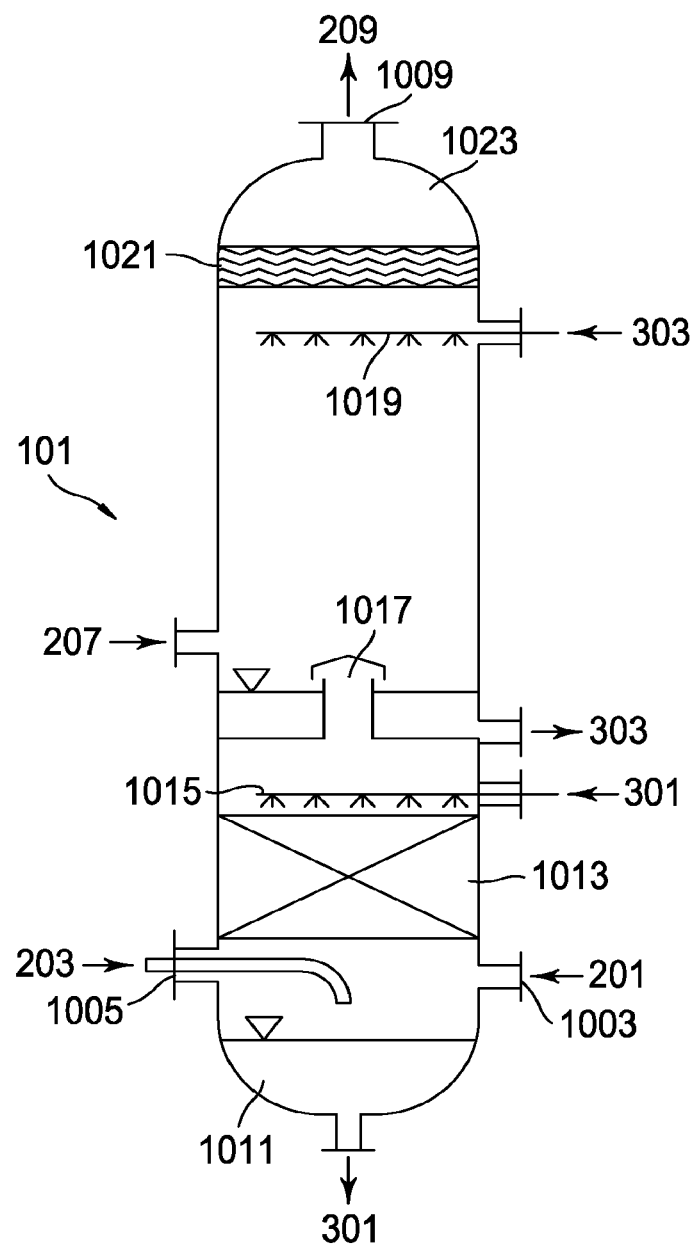

The figures show:

FIG. 1 a schematic diagram of the plant 1 of the invention in one embodiment of the invention and FIG. 2 a schematic diagram of a saturation column 101 in a preferred embodiment.

FIG. 1 shows a schematic diagram of the plant 1 of the invention, the central element of which is the saturation column 101. The saturation column 101 is supplied with an acid water stream 201 via the first feed 1003 and with a process offgas stream 203 via the second feed 1005. A portion of the acid water stream 201, in a first saturation circuit 301, is conducted through a first pump 109 and a first heat transferer 103. This portion of the acid water stream 201 is withdrawn from the bottom 1011 of the saturation column 101.

The saturation column 101 has a two-stage construction; a specific embodiment is described in detail hereinafter with reference to FIG. 2.

A further portion of the acid water stream 201 is fed from the pump 109 as a concentrated acid water stream 207 via a conduit 1007 to the top 1023 of the saturation column 101.

The first heat transferer 103 is coupled to an acid water circuit 305 which is brought in from an absorption column 107 (indicated here merely schematically). The heat from this acid water circuit 305 is waste heat from the absorption column 107 and is introduced into the overall process efficiently by virtue of the process of the invention and the plant 1 of the invention.

Connected to the second stage of the saturation column 101 is a second saturation circuit 303, which is conducted through the second pump 111 and the second heat transferer 105. The second heat transferer 105 is coupled to a heating medium stream in order to introduce heat energy into the second saturation circuit 303.

In the embodiment shown in FIG. 1, downstream of the outlet 1009, a third heat transferer 113 is provided in the offgas stream 209, in order to superheat the offgas stream 209, such that a superheated offgas stream 211 can be fed to a thermal aftertreatment plant not shown in FIG. 1 (optionally with heat recycling, called a "heat recovery unit"). The third heat transferer 113 is heated with steam.

Because of the solvent constituents dissolved in the acid water stream 201 from the workup, for example toluene, diphenyl, diphenyl ether, dimethyl phthalate, the residual liquid can pass through the biphasic region in the course of vaporization. According to the vaporization level, the mixture of water and organic solvent conveyed into the two saturation circuits 301, 303 may also be permanently biphasic.

The formation of a gas phase is not envisaged in the process of the invention, either in the first heat transferer 103 or in the second heat transferer 105. In the two heat transferers 103, 105, the circulating liquid phase is merely heated without being boiled, since the partial pressure-lowering effect is lost through the dilution with an inert gas. Thus, sufficient precaution is taken against the formation of a gas phase.

For the second stage of the saturation column 101, the second heat transferer 105 preferably works as a forced circulation flash evaporator, in order to avoid the formation of a gas phase in the heat transfer apparatus and hence fouling deposits.

FIG. 2 shows a schematic view of the saturation column 101 in a preferred embodiment of the invention. In a first (lower) stage, a bed of random packing 1013 is provided, which is supplied from above with acid water from the first saturation circuit 301 via a feed with a liquid distributor. In addition, the bed of random packing 1013 is supplied with the acid water stream 201. In countercurrent, the process offgas stream 203 from the feed 1005 is passed through the bed of random packing 1013 from a preparation apparatus not shown here.

Via the pump 109, a portion of the acid water is supplied as an enriched acid water stream 207 to the collecting tray of the second stage in the form of a countercurrent spray tower 1017. At the top 1023 of the second stage of the saturation column 101, a liquid phase composed essentially of diphenyl ether is supplied via the feed 1019. At the lower end of the saturation column 101, concentrated acid water is withdrawn from the bottom 1011.

In the top 1023 of the saturation column 101, in this embodiment, a droplet separator 1021 is provided above the second stage, which is cleaned by means of a purge to remove any soiling that arises.

In a preferred embodiment, the diameter of the saturation column 101 is about 4 m; the column height is about 23.5 m.

Table 1 shown below gives detailed values for a specific working example. This gives the specific respective constituents and contents for the individual streams.

| | Stream | | | | | | | | | | |
|---|---|---|---|---|---|---|---|---|---|---|---|
| | 203 [wt. %] | 201 [wt. %] | 301 [wt. %] | 301 [wt. %] | 207 [wt. %] | 209 [wt. %] | 211 [wt. %] | 303 [wt. %] | 303 [wt. %] | 303 [wt. %] | 301 [wt. %] |
| from | | | 101 | 103 | 109 | 101 | 113 | 101 | 111 | 105 | 109 |
| to | 101 | 101 | 109 | 101 | 101 | 113 | | 111 | 105 | 101 | 103 |
| formaldehyde | 0.01 | 4.78 | 0.08 | 0.08 | 0.08 | 0.41 | 0.41 | 0.01 | 0.01 | 0.01 | 0.08 |

-continued

| | Stream | | | | | | | | | | |
|---|---|---|---|---|---|---|---|---|---|---|---|
| | 203 [wt. %] | 201 [wt. %] | 301 [wt. %] | 301 [wt. %] | 207 [wt. %] | 209 [wt. %] | 211 [wt. %] | 303 [wt. %] | 303 [wt. %] | 303 [wt. %] | 301 [wt. %] |
| acrolein | 0.10 | | 0.01 | 0.01 | 0.01 | 0.09 | 0.09 | 0.01 | 0.01 | 0.01 | 0.01 |
| water | 1.36 | 89.19 | 90.93 | 90.93 | 90.93 | 8.76 | 8.76 | 1.12 | 1.12 | 1.12 | 90.93 |
| formic acid | 0.00 | 0.57 | 0.86 | 0.86 | 0.86 | 0.05 | 0.05 | 0.11 | 0.11 | 0.11 | 0.86 |
| acetic acid | 0.07 | 4.30 | 5.58 | 5.58 | 5.58 | 0.42 | 0.42 | 1.20 | 1.20 | 1.20 | 5.58 |
| acrylic acid | 0.10 | 0.94 | 2.13 | 2.13 | 2.13 | 0.17 | 0.17 | 1.74 | 1.74 | 1.74 | 2.13 |
| propionic acid | 0.00 | | 0.00 | 0.00 | 0.00 | 0.00 | 0.00 | 0.00 | 0.00 | 0.00 | 0.00 |
| furfural | 0.00 | | 0.00 | 0.00 | 0.00 | 0.00 | 0.00 | 0.00 | 0.00 | 0.00 | 0.00 |
| benzaldehyde | 0.00 | | 0.00 | 0.00 | 0.00 | 0.00 | 0.00 | 0.00 | 0.00 | 0.00 | 0.00 |
| diacrylic acid | | 0.00 | 0.00 | 0.00 | 0.00 | 0.00 | 0.00 | 0.84 | 0.84 | 0.84 | 0.00 |
| dimethyl phthalate | | 0.22 | 0.38 | 0.38 | 0.38 | 0.02 | 0.02 | 94.97 | 94.97 | 94.97 | 0.38 |
| propene | 0.30 | | 0.00 | 0.00 | 0.00 | 0.28 | 0.28 | 0.00 | 0.00 | 0.00 | 0.00 |
| propane | 0.19 | | 0.00 | 0.00 | 0.00 | 0.18 | 0.18 | 0.00 | 0.00 | 0.00 | 0.00 |
| oxygen | 3.81 | | | | | 3.49 | 3.49 | | | | |
| carbon dioxide | 2.62 | | | | | 2.40 | 2.40 | | | | |
| carbon monoxide | 0.75 | | | | | 0.69 | 0.69 | | | | |
| nitrogen | 90.69 | | | | | 83.05 | 83.05 | | | | |
| Sum total | 100 | 100 | 100 | 100 | 100 | 100 | 100 | 100 | 100 | 100 | 100 |
| Density, kg/m$^3$ | 1.32 | 959.20 | 990.5 | 983.9 | 990.5 | 1.1 | 1.1 | 1070.9 | 1070.9 | 1065.2 | 990.5 |
| Temperature, °C. | 27.30 | 57.90 | 44.8 | 54.8 | 44.8 | 62.7 | 67.7 | 62.7 | 62.7 | 68.4 | 44.8 |
| Pressure, bar | 1.17 | 3.00 | 1.2 | 4.0 | 4.0 | 1.2 | 1.2 | 1.2 | 4.0 | 4.0 | 4.0 |

The thermal balance of this specific working example shows that the first heat transferer 103 is supplied with a power of 3157.5 kW which originates entirely from the waste heat from the absorption column 107. The second heat transferer 105 is supplied with a power of a similar order of magnitude of 3460.9 kW, which originates especially from a steam line. The third heat transferer 113 is supplied with a comparatively low power of 172.5 kW, which is provided by hot condensate.

This specific working example shows that about 50% of the power required can be applied from the waste heat from the absorption column 107 and need not be taken from the steam.

In a comparative experiment, the plant 1 of the invention was modified in such a way that the first saturation circuit 301 was absent and all the heating power had to be introduced via the second heat transferer 105 from steam. For this purpose, 6640.8 kW of power was provided in the second heat transferer, while the same power of 172.6 kW was available in the third heat transferer 113.

In comparison, it was found that the apparatus of the invention saved heating power of 3179.9 kW compared to a plant without the first circuit.

The invention claimed is:

1. A process for treating secondary components obtained in acrolein or (meth)acrylic acid production, the process comprising:
   a) contacting at least one acid water stream comprising at least a portion of water removed in a first stage of a saturation column with at least one process offgas stream;
   b) introducing energy with a first heat transferer provided in a first saturation circuit into the first stage of the saturation column;
   c) partly vaporizing the acid water stream into the process offgas stream to obtain a combined gas stream and passing the combined gas stream into a second stage of the saturation column;
   d) drawing off a concentrated acid water stream from the bottom of the first stage of the saturation column and feeding it to the top of the second stage of the saturation column;
   e) introducing energy with a second heat transferer provided in a second circuit into the second stage of the saturation column;
   f) partly vaporizing the concentrated acid water stream into the combined gas stream to obtain an offgas stream;
   g) superheating the offgas stream, after it has been saturated, in a third heat transferer to obtain a superheated offgas stream; and
   h) transferring the offgas stream or the superheated offgas stream from the saturation column to a thermal aftertreatment.

2. The process according to claim 1, wherein energy is introduced in step b) by coupling the first heat transferer with a stream present in the process for acrolein or (meth)acrylic acid production.

3. The process according to claim 2, wherein the stream present in the process for acrolein or (meth)acrylic acid production is an acid water circulation stream from an absorption column.

4. The process according to claim 2, wherein the stream present in the process for acrolein or (meth)acrylic acid production is a circulation stream from a condensation circuit of a distillation column.

5. The process according to claim 1, wherein energy is introduced in step e) by coupling the second heat transferer with a heating medium stream.

6. The process according to claim 1, wherein, in step c), at least 20% of the wastewater stream is vaporized.

* * * * *